United States Patent [19]

Kiel

[11] Patent Number: 6,046,365

[45] Date of Patent: *Apr. 4, 2000

[54] PROCESS FOR PREPARING CYCLOHEXANONES BY HYDROGENATION OF THE CORRESPONDING PHENOLS (I.)

[75] Inventor: Wolfgang Kiel, Odenthal, Germany

[73] Assignee: Bayer Aktiengesellschaft

[*] Notice: This patent is subject to a terminal disclaimer.

[21] Appl. No.: 09/106,814

[22] Filed: Jun. 29, 1998

[30] Foreign Application Priority Data

Jun. 30, 1997 [DE] Germany .......................... 197 27 712

[51] Int. Cl.⁷ .................................................. C07C 45/00
[52] U.S. Cl. ........................... 568/362; 568/309; 568/376
[58] Field of Search ..................... 568/308, 309, 568/325, 326, 327, 329, 330, 338, 362, 376, 403

[56] References Cited

U.S. PATENT DOCUMENTS

| | | | |
|---|---|---|---|
| 2,829,166 | 4/1958 | Joris et al. | 260/586 |
| 3,076,810 | 2/1963 | Duggan et al. | 260/586 |
| 3,998,884 | 12/1976 | Gibson | 260/586 P |
| 4,200,553 | 4/1980 | Van Peppen et al. | 252/447 |
| 4,304,943 | 12/1981 | Bjornson | 568/361 |

FOREIGN PATENT DOCUMENTS

| | | |
|---|---|---|
| 0731075 A1 | 9/1996 | European Pat. Off. . |
| 2372136 | 6/1978 | France . |
| 1144267 | 2/1963 | Germany . |
| 2530759 B1 | 6/1976 | Germany . |
| 2752291 A1 | 6/1978 | Germany . |
| 2909780 | 9/1980 | Germany . |
| 2909780 A1 | 9/1980 | Germany . |
| 1512497 | 6/1978 | United Kingdom . |
| 1563044 | 3/1980 | United Kingdom . |

OTHER PUBLICATIONS

Nishimura et al, Bull. Chem.Soc.Jpn., 65, 2955–2959, 1992.

"Substitute cyclohexanone produce substitute phenol hydrogenolysis water palladium catalyst intermediate pharmaceutical cardiovascular agent" abstract of JP 57004932, 1982.

Primary Examiner—Sreeni Padmanabhan
Attorney, Agent, or Firm—Brinks Hofer Gilson & Lione

[57] ABSTRACT

Unsubstituted or substituted cyclohexanones are advantageously prepared by hydrogenation of the corresponding phenols in the presence of a palladium-on-carbon catalyst at from 100 to 250° C. and from 1 to 20 bar of hydrogen pressure if the catalyst is mixed with a base component and from 20 to 200% by weight of water (based on the base component) and this mixture is used in the hydrogenation. For identical batches, this gives virtually identical hydrogenation times and virtually equally good yields of cyclohexanones.

17 Claims, No Drawings

PROCESS FOR PREPARING CYCLOHEXANONES BY HYDROGENATION OF THE CORRESPONDING PHENOLS (I.)

BACKGROUND OF THE INVENTION

The present invention relates to an advantageous process for the hydrogenation of phenols to give the corresponding cyclohexanones using palladium-on-carbon catalysts.

Processes for the hydrogenation of phenols over palladium-on-carbon catalysts to give cyclohexanones are known in principle (see, for example, DE-A 2 909 780, DE-A 2 530 759 and U.S. Pat. No. 2,829,166).

In general, to achieve a good selectivity, a hydrogen pressure of less than 20 bar and a reaction temperature in the range from 120 to 250° C. are sought and an alkaline compound is added to the hydrogenation mixture. The catalyst can, if desired, be treated with alkali metal ions such as Na or K ions (see, for example, German Auslegeschrift 1 144 267 (U.S. Pat. No. 3,076,810)). The use of phenoxides and bicarbonates is described in FR-A 2 372 136 (G.B. 1,563,044)).

According to DE-A 2 909 780, sodium carbonate, borax and/or sodium acetate are used for the hydrogenation of p-tert-amylphenol. At the same time, it is indicated here that the use of palladium catalysts having metal surface areas of 15 m$^2$/g and more is promising. Preference is given to using palladium-on-carbon catalysts containing 5% by weight of palladium, based on a support which has a surface area of 800 m$^2$/g.

When using these known processes, in particular when they are extended to further substituted phenols, it is found that the hydrogenation results (e.g. yield of desired cyclohexanones) and the hydrogenation times required fluctuate greatly in repeat batches under the same conditions (see Examples 14 to 19).

Since, in many cases, cyclohexanones are used as starting compounds for pharmaceuticals and crop protection agents, a high purity has to be ensured. Especially in the case of difficult-to-remove secondary components, the value of a preparative process therefore depends on the achievement of a very high selectivity together with good reproducibility of the results. Furthermore, greatly varying hydrogenation results and times result in problems in carrying out the reaction and in the work-up of the reaction mixtures.

SUMMARY OF THE INVENTION

The invention is therefore based on the object of making cyclohexanones by hydrogenation of the corresponding phenols (I).

DESCRIPTION OF THE INVENTION

A process has now been found for preparing cyclohexanones of the formula (I)

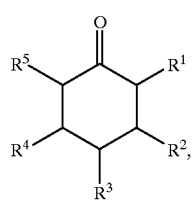

where $R^1$, $R^2$, $R^3$, $R^4$ and $R^5$ are each, independently of one another, hydrogen, hydroxy, $C_1$–$C_{10}$-alkyl, $C_3$–$C_6$-cycloalkyl, $C_6$–$C_{10}$-aryl, $C_6$–$C_{10}$-aryl—$CH_2$—, $C_6$–$C_{10}$-aryl—O—, $C_1$–$C_{10}$-alkoxy, $C_3$–$C_8$-cycloalkoxy, $C_1$–$C_4$-alkylamino, di-$C_1$–$C_4$-alkylamino, $C_1$–$C_4$-acylamino, COOR$^6$ where $R^6$=hydrogen or $C_1$–$C_4$-alkyl or $R^7$—$CH_2$— where $R^7$=hydroxy, $C_1$–$C_4$-alkoxy, $C_1$–$C_4$-alkylamino or di-$C_1$–$C_4$-alkylamino, by hydrogenation of phenols of the formula (II)

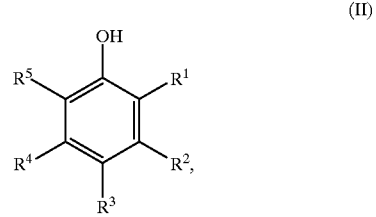

where $R^1$ to $R^5$ are as defined for formula (I),
in the presence of a palladium-on-carbon catalyst at from 100 to 250° C. and from 1 to 20 bar of hydrogen pressure, wherein the catalyst is mixed with a base component and from 20 to 200% by weight of water (based on the base component) and this mixture is used in the hydrogenation.

In the formulae (I) and (II), $R^1$, $R^2$, $R^3$, $R^4$ and $R^5$ preferably represent, independently of one another, hydrogen, hydroxy, $C_1$–$C_6$-alkyl, $C_1$–$C_6$-alkoxy or $C_1$–$C_4$-acylamino. It is also preferred that from 1 to 4 of the radicals $R^1$ to $R^5$ are different from hydrogen.

Examples of $C_1$–$C_6$-alkyl are methyl, ethyl, i-propyl, t-butyl and pentyl. Examples of $C_1$–$C_6$-alkoxy are methoxy, ethoxy and i-propoxy. An example of $C_1$–$C_4$-acylamino is acetylamino.

Particularly preferably, $R^1$, $R^2$, $R^4$ and $R^5$ represent hydrogen and $R^3$ represents hydroxy, $C_1$–$C_6$-alkyl, $C_1$–$C_6$-alkoxy or $C_1$–$C_4$-acylamino.

The palladium-on-carbon catalysts can comprise, for example, from 1 to 15% by weight of palladium on any carbon. These catalysts preferably contain from 2 to 12% by weight of palladium. Such catalysts are commercially available. They are frequently supplied in a form which is moist with water and can also be used in this form which is moist with water. Based on the phenol of the formula (II), it is possible to use, for example, from 0.001 to 1% by weight of catalyst (calculated as Pd metal). This amount is preferably from 0.05 to 0.2% by weight.

The reaction temperature is preferably from 150 to 200° C. and the hydrogen pressure is preferably from 3 to 8 bar.

An essential feature of the present invention is that the catalyst is not used as such or in a form which is moist with water, but it is mixed beforehand with a base component and from 20 to 200% by weight of water (based on the base component). Suitable base components are, in particular, alkali metal salts which have a basic reaction in aqueous medium. Preference is given to borax ($Na_2B_4O_7 \cdot 10H_2O$), sodium acetate and disodium hydrogen phosphate. Based on the palladium-on-carbon catalyst, it is possible to use, for example, from 5 to 50% by weight of base component. This amount is preferably from 10 to 20% by weight.

Based on the base component, the amount of water is preferably from 50 to 150% by weight. The amount of water to be used does not include any water of crystallization present in the base component. Likewise, any water which has been used for moistening the catalyst to give safer handling is not taken into account. It is advantageous first to mix the base component with water, with it being of no consequence whether the base component dissolves completely or not, and then to mix the base component/water mixture with the dry or moist palladium-on-carbon catalyst.

The process of the invention can be carried out in the presence or absence of solvents. If the phenol of the formula (II) which is used has a melting point below the hydrogenation temperature, preference is given to carrying out the reaction using molten phenol of the formula (II) without addition of solvents. When using phenols of the formula (II) which have higher melting points, it is necessary to add a solvent, for example an alcohol or ether.

The process of the invention can be carried out, for example, in stirred, tube or loop reactors.

The process of the invention has the advantages that the hydrogenation times for identical batches are virtually identical and that under identical conditions it gives the desired cyclohexanones of the formula (I) selectively in always virtually equally good yields. Both lead to high cost savings in the work-up of the reaction mixtures.

EXAMPLES

Examples 1 to 5

0.5 g of borax and 0.5 g of water were mixed and 6 g of a catalyst which was moist with water (water content=50% by weight) and comprised 5% by weight of palladium on carbon were then mixed in. The resulting mixture was added to 300 g of molten p-tert-butylphenol and this reaction mixture was hydrogenated in a tube reactor at from 150 to 180° C. and from 3 to 8 bar of hydrogen pressure until no more hydrogen was absorbed. Five batches (=Examples 1 to 5) were reacted in succession. The results are shown in Table 1.

TABLE 1

| Example No. | Hydrogenation time (min) | p-tert-Butylcyclohexanone content of the reaction mixture (% by weight) |
|---|---|---|
| 1 | 83 | 93.2 |
| 2 | 89 | 92.2 |
| 3 | 85 | 91.4 |
| 4 | 88 | 91.8 |
| 5 | 83 | 91.7 |

Examples 6 and 7

The procedure of Example 1 was repeated, but using 0.5 g of disodium hydrogen phosphate (Example 6) or 0.5 g of sodium acetate (Example 7) in place of borax. The results are shown in Table 2 in which Example 1 is again reproduced.

TABLE 2

| Example No. | Base component | Hydrogenation time (min) | p-tert-Butylcyclohexanone content of the reaction mixture (% by weight) |
|---|---|---|---|
| 1 | Borax | 83 | 93.2 |
| 6 | $Na_2HPO_4$ | 48 | 88.0 |
| 7 | $CH_3COONa$ | 41 | 90.1 |

Examples 8 to 13

The procedure of Example 1 was repeated, but 6 g of a catalyst which was moist with water (water content=50% by weight) and comprised 10% by weight of palladium on carbon was used (Example 8). The catalyst was then separated off and reused in a batch under the same conditions. This reuse was carried out a total of 5 times in succession (Examples 9 to 13). The results are shown in Table 3 which again reproduces Example 1.

TABLE 3

| Example No. | Catalyst (% by weight of Pd on carbon) | Hydrogenation time (min) | p-tert-Butylcyclohexanone content of the reaction mixture (% by weight) |
|---|---|---|---|
| 1 | 5 | 83 | 93.2 |
| 8 | 10 | 52 | 90.6 |
| 9 | 10 | 46 | 91.3 |
| 10 | 10 | 44 | 92.3 |
| 11 | 10 | 44 | 91.2 |
| 12 | 10 | 42 | 92.1 |
| 13 | 10 | 40 | 90.1 |

Examples 14 to 19 (for comparison)

The procedure of Example 1 was repeated, but borax without water and the catalyst were separately introduced into molten p-tert-butylphenol. Six batches were reacted in succession under identical conditions. The results are shown in Table 4.

TABLE 4

| Example No. | Hydrogenation time (min) | p-tert-Butylcyclohexanone content of the reaction mixture (% by weight) |
|---|---|---|
| 14 | 51 | 91.4 |
| 15 | 32 | 86.5 |
| 16 | 224 | 83.7 |
| 17 | 72 | 90.6 |
| 18 | 92 | 29.2 |
| 19 | 1126 | 64.6 |

I claim:
1. A process for preparing a cyclohexanone of the formula (I):

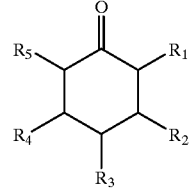

wherein $R^1$, $R^2$, $R^3$, $R^4$ and $R^5$ are each, independently of one another, hydrogen, hydroxyl, $C_1$–$C_{10}$-alkyl, $C_3$–$C_6$-cycloalkyl, $C_6$–$C_{10}$-aryl, $C_6$–$C_{10}$-aryl—$CH_2$—, $C_6$–$C_{10}$-aryl—O—, $C_1$–$C_{10}$-alkoxy, $C_3$–$C_8$-cycloalkoxy, $C_1$–$C_4$-alkylamino, di-$C_1$–$C_4$-alkylamino, $C_1$–$C_4$-acylamino, $COOR^6$ where $R^6$ is hydrogen or $C_1$–$C_4$-alkyl or $R^7$—$CH_2$— where $R^7$ is hydroxyl, $C_1$–$C_4$-alkoxy, $C_1$–$C_4$-alkylamino or di-$C_1$–$C_4$-alkylamino;

comprising:
(a) forming a catalyst mixture of palladium-on-carbon catalyst, a base component, and from 20 to 200% by weight of water, based on the base component to form a catalyst mixture, and (b) hydrogenating a phenol of the formula (II);

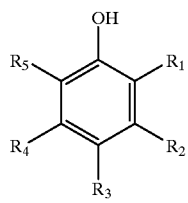

wherein (a) is performed before (b), and
wherein $R^1$, $R^2$, $R^3$, $R^4$ and $R^5$ are defined above, in the presence of the catalyst mixture at from 100 to 250° C. and from 1 to 20 bar of hydrogen pressure.

2. The process as claimed in claim 1, wherein, in the formulae (I) and (II), $R^1$, $R^2$, $R^3$, $R^4$ and $R^5$ represent, independently of one another, hydrogen, hydroxy, $C_1$–$C_6$-alkyl, $C_1$–$C_6$-alkoxy or $C_1$–$C_4$-acylamino and from 1 to 4 of the radicals $R^1$ to $R^5$ are different from hydrogen.

3. The process as claimed in claim 1, wherein, in the formulae (I) and (II), $R^1$, $R^2$, $R^4$ and $R^5$ represent hydrogen and $R^3$ represents hydroxy, $C_1$–$C_6$-alkyl, $C_1$–$C_6$-alkoxy or $C_1$–$C_4$-acylamino.

4. The process as claimed in claim 1, wherein the palladium-on-carbon catalyst contains from 1 to 15% by weight of palladium.

5. The process as claimed in claim 1, wherein, based on the phenol of the formula (II), from 0.001 to 1% by weight of catalyst (calculated as Pd metal) is used.

6. The process as claimed in claim 1, wherein the base component used is borax, sodium acetate or disodium hydrogen phosphate.

7. The process as claimed in claim 1, wherein the amount of base component is from 5 to 50% by weight, based on the palladium-on-carbon catalyst.

8. The process as claimed in claim 1, wherein the amount of water is from 50 to 150% by weight, based on the base component.

9. The process as claimed in claim 1, wherein the base component is first mixed with water to form a base component/water mixture, and the base component/water mixture, is then mixed with the palladium-on-carbon catalyst.

10. The process as claimed in claim 1, wherein hydrogenation of phenols of the formula (II) occurs at a reaction temperature of from 150 to 200° C.

11. The process as claimed in claim 1, wherein hydrogenation of the phenols of the formula (II) occurs at a hydrogen pressure from 3 to 8 bar.

12. The process as claimed in claim 1, wherein the base component used is an alkali metal salt.

13. The process as claimed in claim 1, wherein hydrogenation occurs in a stirred, tube, or loop reactor.

14. The process as claimed in claim 1, wherein the amount of base component is of from 10 to 20% by weight, based on the palladium-on-carbon catalyst.

15. The process as claimed in claim 1, wherein the process is carried out in the absence of a solvent where the phenol of the formula (II) has a melting point below the hydrogenation temperature.

16. The process as claimed in claim 1, wherein the process is carried out in the presence of a solvent where the phenol of the formula (II) has a melting point above the hydrogenation temperature.

17. The process as claimed in claim 16, wherein the solvent used is an alcohol or ether.

* * * * *